US006513369B1

(12) United States Patent
Chew

(10) Patent No.: US 6,513,369 B1
(45) Date of Patent: Feb. 4, 2003

(54) IN-SITU NON-DESTRUCTIVE ELASTIC RECOVERY TESTER

(75) Inventor: Yit-Lin Michael Chew, Kent Ridge Crescent (SG)

(73) Assignee: The National University of Singapore, Kent Ridge Crescent (SG)

( * ) Notice: Subject to any disclaimer, the term of this patent is extended or adjusted under 35 U.S.C. 154(b) by 0 days.

(21) Appl. No.: 09/787,302

(22) PCT Filed: Sep. 3, 1999

(86) PCT No.: PCT/SG99/00092

§ 371 (c)(1),
(2), (4) Date: Jun. 19, 2001

(87) PCT Pub. No.: WO00/17621

PCT Pub. Date: Mar. 30, 2000

(30) Foreign Application Priority Data

Sep. 19, 1998 (SG) ............................................ 9802863

(51) Int. Cl.[7] ................................................ G01N 3/48
(52) U.S. Cl. ......................................................... 73/81
(58) Field of Search ............................... 73/78, 79, 81, 73/82, 84, 85, 87, 813, 818, 825

(56) References Cited

U.S. PATENT DOCUMENTS

| | | | | |
|---|---|---|---|---|
| 3,955,404 A | * | 5/1976 | Bickel et al. | 73/573 |
| 4,492,111 A | * | 1/1985 | Kirkland | 324/323 |
| 4,596,773 A | * | 6/1986 | Wheeler, Jr. | 435/287.4 |
| 4,691,559 A | * | 9/1987 | Fischer | 73/81 |
| 5,663,649 A | * | 9/1997 | Topp et al. | 324/643 |
| 6,289,734 B1 | * | 9/2001 | Daugela | 73/573 |

FOREIGN PATENT DOCUMENTS

| | | |
|---|---|---|
| GB | 2167568 A | 5/1986 |
| SU | 1226143 A | 9/1984 |
| SU | 1434318 A1 | 10/1986 |

* cited by examiner

*Primary Examiner*—Max Noori
(74) *Attorney, Agent, or Firm*—Birch, Stewart, Kolasch & Birch, LLP

(57) ABSTRACT

A method for the non-destructive, in-situ assessment of a resilient elastic substrate, said method comprising the steps of: applying detector means to a surface of said substrate; urging said detector means into said substrate at a substantially constant speed to a predetermined depth; holding said detector means at said predetermined depth for a predetermined time; releasing said detector means, allowing elastic recovery of said substrate; and processing compressibility and/or elastic recovery of said substrate during said urging, holding and/or releasing steps. An elastic recovery testing assembly for the non-destructive, in-situ assessment of a resilient elastic substrate, said assembly comprising: detector means adapted to be applied to a surface of said substrate and urged into said substrate at a substantially constant speed and held in said substrate at a predetermined depth for a predetermined time; actuating means for actuating said urging of said detector means into said substrate; and processing means for storing and/or processing compressibility and/or elastic recovery of said substrate.

23 Claims, 2 Drawing Sheets

IN-SITU NON-DESTRUCTIVE ELASTIC RECOVERY TESTER

This application is the national phase under 35 U.S.C. § 371 of PCT International Application No. PCT/SG99/00092 which has an International filing date of Sep. 3, 1999, which designated the United States of America and was published in English.

FIELD OF THE INVENTION

The present invention relates to a method and apparatus for the non-destructive, on-site assessment of the performance of resilient elastic substrates. In particular, the present invention relates to the assessment of, for example, sealants on building facades.

BACKGROUND OF THE INVENTION

For convenience, the background of the invention will be discussed with reference to a particularly suitable field of application of the method and apparatus of the invention—the assessment of sealants. Corresponding art for other resilient elastic substrates will be readily determined by those skilled in the art.

The predisposition for all year round air-conditioning and the ever increasing energy cost, coupled with the high level of prefabrication in construction, have increased the role played by sealants in building joints. Effective sealants are important in contributing to successful watertight building envelopes and preventing infiltration of air. The high cost of energy for air-conditioning and problems associated with water infiltration are rendering the serious consideration of building sealants essential. The long term financial impact of poor sealants on the cost of keeping the building comfortable is now also being calculated by building owners.

Sealants have conventionally been widely used in building and civil engineering works as they serve several general functions as follows:

(a) Waterproofing Function

Sealants are used as components of complete waterproofing system by resisting the passage of water into the jointing part of the building.

(b) Environmental function

Sealants are used as barriers to resist the passage of heat, light, sound, odour, dust, etc. into the building.

(c) Movement Control Function

Sealants are used to accommodate continuing changes in size of the joint due to thermal, moisture and structural movements, including vibration and creep.

A sealant must be able to perform these functions, and at the same time it must have acceptable appearance and durability, be economically acceptable, and have acceptable maintenance costs. In some cases, additional functions may also be required such as ability to perform under special temperature or humidity conditions and ability to withstand polluted atmosphere.

The performance of sealants depends to a large extent on the proper selection according to the environment to which the sealant is to be exposed, and is influenced by the workmanship and methods of application on site. Sealants are generally expensive to install and remove, and thus replacement costs may be high even though the sealant itself as a material may be relatively inexpensive.

In recent years, the deterioration of sealants has attracted much attention in conjunction with the construction industry's increasing use of large panel curtain walls. Many sealants in high rise buildings are reaching the limit of their life span. To derive an efficient repair/maintenance strategy for a large area such as in the case of a building facade, an efficient on-site non-destructive diagnostic technique is essential. Temporary work in the diagnostic process must be minimised. At present, no such scientific method is available. The conventional techniques are generally based on tedious, destructive, slow laboratory based methodologies.

In the case of determining the durability and performance of new sealants, the conventional testing techniques generally stipulates that the sealant must be statically cured for a period of 28 days before the tests are to be conducted. This seems to suggest that the accentuation when it comes to selection of suitable sealants for a particular job is on how it will perform under weathering, ignoring the fact that failure may actually occur before the sealant has a chance to cure. In practice, sealants which are installed on-site, do not "enjoy" the luxury of being statically cured in a fixed position, before experiencing undue stress caused by movements. They are subjected to dynamic curing rather than static curing and occurrences of premature failures are highly possible. This highlights the concern that conventional control tests conducted may be meaningless if sealants were to fail before they are put to service. It is thus important to monitor the in-service performance of sealants regularly especially during the initial stage after application. To achieve that, a reliable on-site, non-destructive diagnostic technique is needed.

The present invention advantageously provides a method and apparatus for the accurate, quick and non-destructive, assessment of the performance of resilient elastic substrates, such as sealants, for example on building facades, on-site. It is envisaged that such a method and apparatus may be applicable in the fields of maintenance and repair of building facades, performance assessment and diagnosis, and quality control in manufacturing and on-site applications.

SUMMARY OF THE INVENTION

According to one aspect of the invention there is provided a method for the non-destructive, in-situ assessment of a resilient elastic substrate, the method comprising the steps of:

- applying detector means to a surface of the substrate;
- urging the detector means into the substrate at a substantially constant speed to a predetermined depth;
- holding the detector means at the predetermined depth for a predetermined time;
- releasing the detector means, allowing elastic recovery of the substrate; and
- processing compressibility and/or elastic recovery of the substrate during the urging, holding and/or releasing steps.

The application of the detector means to the surface of the substrate, urging of the detector means into the substrate, holding of the detector means at the predetermined depth, and releasing of the detector means may be manually or automatically controlled. Furthermore, the speed at which the detector means is urged to the predetermined depth, the predetermined depth and the predetermined time may be determined based on the particular substrate being assessed. However, in a preferred embodiment the detector means is urged into the substrate at a speed of from about 0.3 to about 0.7 mm/s, more preferably at a constant speed of about 0.5 mm/s. Further, it is preferred that the detector means be held at the predetermined depth for a period of at least about 5 seconds. The predetermined depth will generally be no more than about 10 mm, and is preferably about 5 mm.

According to a preferred embodiment, the releasing step comprises maintaining the detector means in engagement with the surface of the substrate for a period of about 5 seconds or more after the release and during elastic recovery of the substrate. The maintaining of engagement of the detector means for at least 5 seconds during elastic recovery of the substrate advantageously enables the attainment of the most representative recovery values for the substrate. That is, the rate of change (i.e. change in elastic recovery with time) within the first 5 seconds after the release of the detector means is the most relevant to the assessment of the performance of the substrate. It will be readily understood that in some cases the rate of recovery after 5 seconds, such as within about 2 hours after the compression of the substrate, may be of interest. Such instances are also envisaged within the scope of the present invention.

While the assessment of the substrate by the above method may provide sufficient information to accurately and efficiently assess the performance of the substrate, further assessment may be made by other means. For example, in one embodiment the method further comprises, on the removal of the detector means from the surface of the substrate, visually inspecting the surface of the substrate to which the detector means has been applied. A detailed visual examination during testing may also be facilitated in order to monitor adhesion and cohesion of the substrate.

According to another aspect of the invention there is provided an elastic recovery testing assembly for the non-destructive, in-situ assessment of a resilient elastic substrate, said assembly comprising:

- detector means adapted to be applied to a surface of said substrate and urged into said substrate at a substantially constant speed and held in said substrate at a predetermined depth for a predetermined time;
- actuating means for actuating said urging of said detector means into said substrate; and
- processing means for storing and/or processing compressibility and/or elastic recovery of said substrate.

Once again, the speed at which the detector means is urged into the substrate, the predetermined depth and the predetermined time may be determined based on the substrate being assessed. Furthermore, the application of the detector means to the substrate, including the urging of the detector means into the substrate, and holding of the detector means in contact with the substrate may be manually or automatically controlled. In a preferred embodiment, the detector means is adapted to be urged into the substrate at a substantially constant speed of from about 0.3 to about 0.7 mm/s, more preferably about 0.5 mm/s. The detector means is also preferably adapted to be held in the substrate at a depth of no more than about 10 mm, preferably about 5 mm.

After the detector means has been held at the predetermined depth for the predetermined time, the actuating means may automatically disengage the detector means, or may be manually disengageable. In any event, the actuating means is preferably disengageable such that, in use when the actuating means is disengaged, the detector means is displaceable by the substrate due to elastic recovery of the substrate. In this instance, as discussed in accordance with the method of the invention above, the detector means is preferably maintained in contact with the surface of the substrate for a period of at least about 5 seconds after the actuating means is disengaged so that recovery values may be attained to facilitate an accurate assessment of the performance of the substrate.

According to a preferred embodiment, the assembly further comprises visual assessment means for facilitating visual assessment of the surface of the substrate to which the detector means has been applied. Advantageously, the visual assessment means may also be used for a detailed visual examination of the surface during testing. Preferably, the visual assessment means comprises a microscope unit mounted on the assembly.

The detector means may comprise any suitable means for application to the surface of the substrate. However, in a preferred embodiment the detector means comprises a detector head which contacts the surface of the substrate, and a piston shaft adapted to be engaged by the actuating means and for urging the detector head into the substrate. More preferably, the detector head is a brass pellet having a width of about 4 millimeters or more. It will be readily understood that the width of the detector head will be determined based on the particular application of the assembly. For example, if the assembly is being used to test a sealant in the joint of a building facade, the detector head will be of a width which may be suitably applied taking into consideration the width of the joint of the facade.

Similarly, the actuating means may comprise any suitable form which may be manually or automatically operable by a user of the assembly. According to one embodiment the actuating means comprises a piston load controller which is manually operable by a user of the assembly to urge the detector means into the substrate.

If the assembly is manually operable, it is preferred that the assembly further comprise prompting means for prompting a user of the assembly. For example, the prompting means may prompt a user of the assembly to increase or decrease the speed at which the detector means is being urged into the substrate. The prompting means may also prompt a user of the assembly to hold the detector means at the predetermined depth, release the detector means to allow the elastic recovery of the substrate, and/or maintain the detector means in contact with the surface of the substrate during elastic recovery of the substrate. The prompting means may comprise any suitable prompt for said user. This may, for example, be a visual or audio prompt. Preferably, the prompting means comprises an electronic display.

The processing of data during use of the assembly may be achieved by any suitable means. Furthermore, data may be simply stored by the assembly for later interpretation using, for example, a computer interface. Preferably, the processing means comprises an electronic transducer or potentiometer which engages the detector means and a load cell which allow instantaneous detection of compressibility and/or elastic recovery of the substrate. As such, in use the assembly advantageously provides a readout which may be recorded and/or interpreted by a user of the assembly. Advantageously the assembly facilitates interfacing with a printer, computer or data logger for detailed data logging of compressibility and/or elastic recovery of the substrate.

The assembly is advantageously a small, light, portable instrument designed for non-destructive, in-situ measurements of the performance of, for example, sealants based on elastic recovery and compressibility.

BRIEF DESCRIPTION OF THE DRAWINGS

An embodiment of the present invention will now be described in more detail with reference to the accompanying drawings in which.

Figure 1:
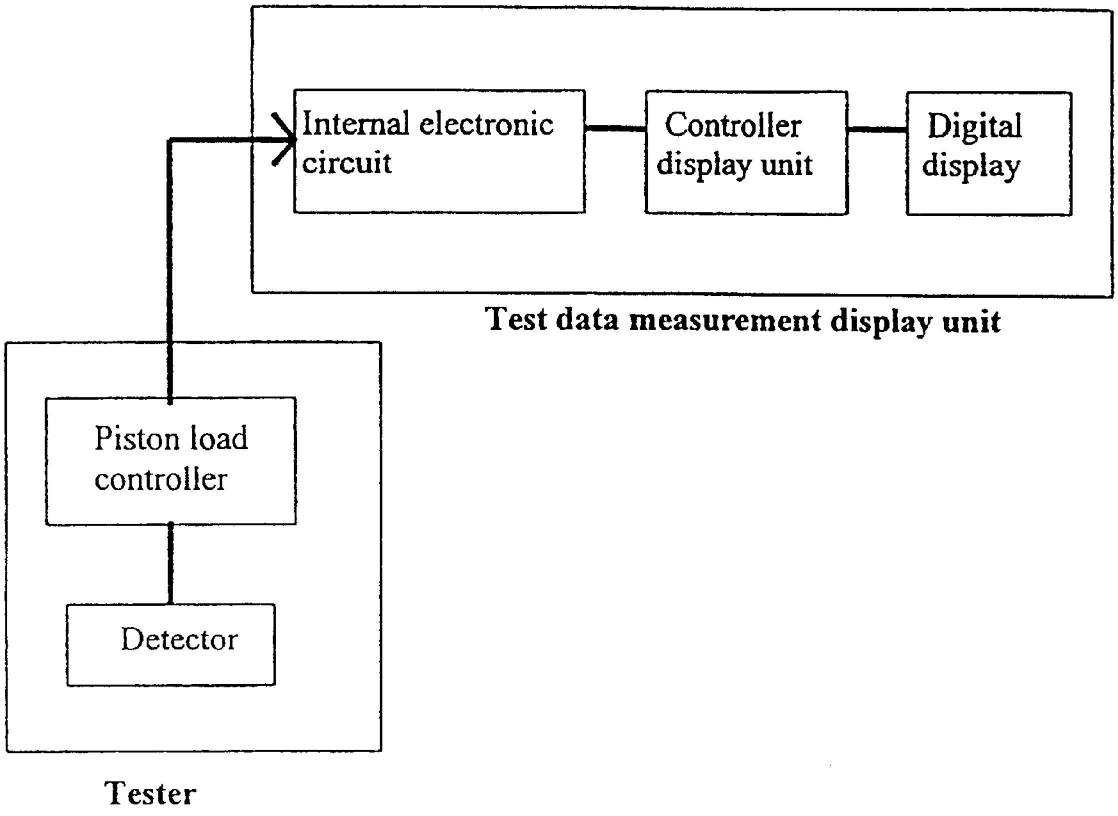
FIG. 1 illustrates a schematic block diagram of the assembly, consisting of a tester and a test data measurement display unit.
Figure 2:
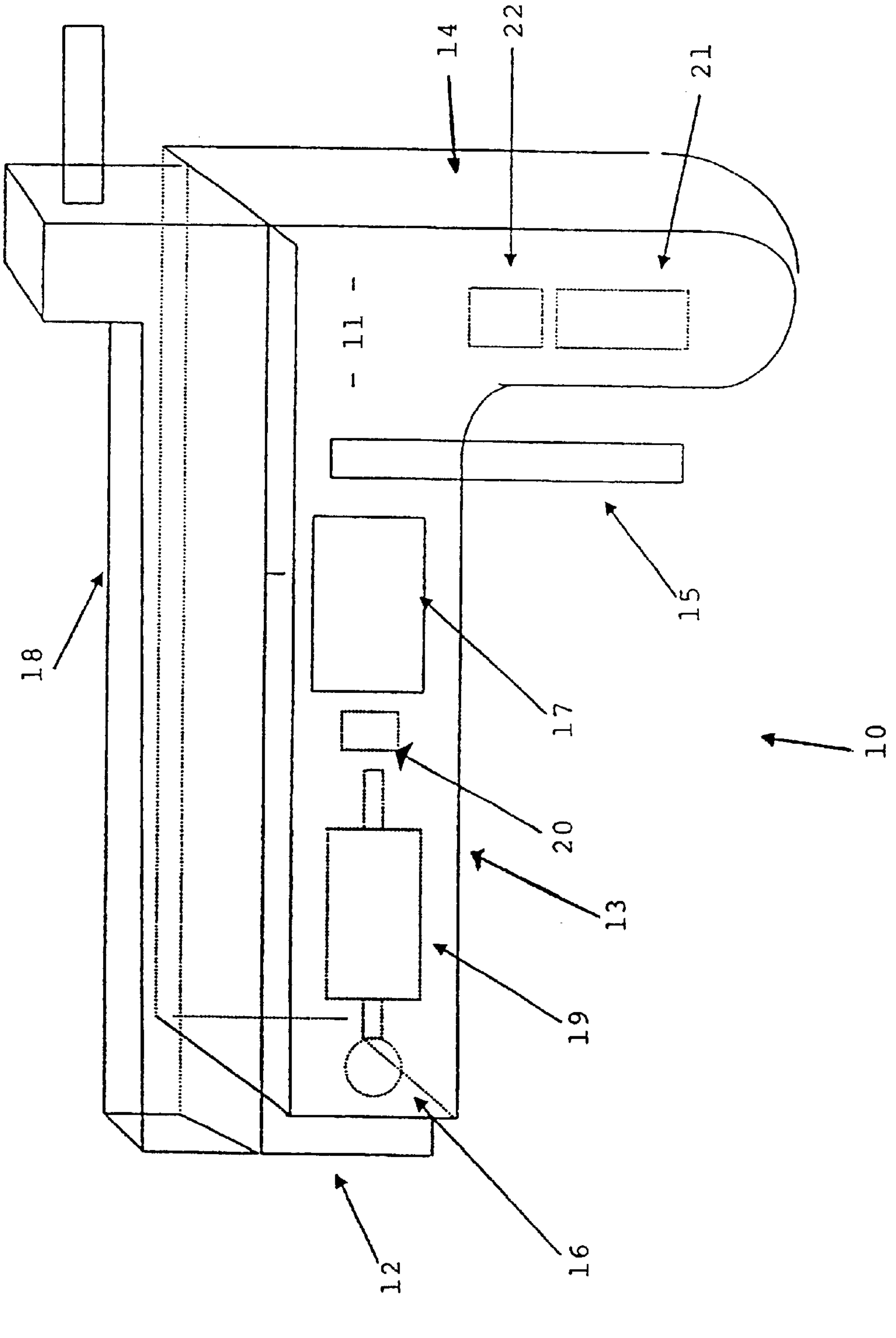
FIG. 2 illustrates a schematic diagram of the assembly.

The following detailed description of the invention will be discussed in relation to the particular application of the method and apparatus of the invention to the assessment of sealants, but should not be considered to be in any way restrictive on the claims.

The elastic recovery testing assembly 10 is substantially in the form of a gun and comprises a mounting 11, an end surface of which, in use, is applied to a wall such that it bridges a joint filled with the sealant to be tested. In particular, the end surface 12 is applied to the wall on both sides of the joint.

The weight of the assembly 10 is supported with one hand of the user by holding the base 13 of the assembly 10. The other hand of the user holds the handle 14 of the assembly 10.

Once the assembly 10 is in place, the end surface 12 engaging the wall on both sides of the joint to be assessed, a piston load controller 15 is actuated by the user by squeezing with the fingers of the hand holding the handle 14.

As the controller 15 is squeezed by the user, a detector 16 is urged into the surface of the sealant in the joint. The rate at which the detector 16 is urged into the sealant will be relative to the rate at which the controller 15 is squeezed by the user of the assembly 10. Generally, the rate at which the detector 16 is urged into the sealant will be approximately 0.5 mm/s. If the rate at which the user is squeezing controller 15 is too high or too low, an electronic display 17 will prompt the user to decrease or increase the rate at which the controller 15 is being displaced respectively.

Once a maximum predetermined depth has been reached by the detector 16, the assembly 10 will beep and the electronic display 17 will prompt the user of the assembly 10 to wait. The user will thus maintain the controller 15 at the predetermined maximum until the electronic display 17 prompts the user to release the controller 15. When the user releases the controller 15, the electronic display 17 will prompt the user to wait once again. At this stage, the end surface 12 of the assembly 10 will be maintained in contact with the wall, and the detector 16 will be displaced due to elastic recovery of the sealant in the joint. The time for which the detector 16 is maintained at a predetermined maximum is at least 5 seconds. Further, the time for which the end surface 12 is maintained in contact with the wall surface following the release of the controller 15 is at least 5 seconds. After 5 seconds has elapsed since the release of the controller 15 by the user of the assembly 10, the end surface 12 may be removed from the wall surface.

On removal of the assembly from the wall, the measurement of elastic recovery in millimeters or percentage and the maximum compressibility in Newton will be displayed on the electronic display 17.

Visual examination of the tested surface of the sealant in the joint may be conducted using a microscope unit 18 mounted on the assembly 10. This may show defects such as adhesive and cohesive cracks. Further, such a visual examination using the microscope unit 18 may also be conducted during the application of the detector 16 to the surface of the sealant.

The compression and elastic recovery values are processed and determined using an electronic transducer or potentiometer 19 which engages a shaft of the detector 16 in combination with a load cell 20. As suggested above, the results may be displayed by the electronic display 17 provided by the assembly 10. Alternatively, the assembly 10 may be provided with interfacing abilities for interfacing with a printer, computer or data logger for detailed data logging of compression and elastic recovery results.

The assembly 10 may be powered by an electrical connection. However, as illustrated, the handle 14 of the assembly 10 advantageously encloses a battery 21 and rheostat 22 to facilitate portable operation of the assembly 10.

The applicability of the tester in the building and construction industry is obvious. Interested parties are building owners, authorities, building professionsals, diagnostic specialists, supervisors/inspectors, suppliers and the like for the monitoring of the performance of sealants non-destructively and with ease. The fields of application are:

(1) Maintenance and repair (2) Assessment and diagnosis (3) Quality control in sealant formulation, manufacturing as well as application on site (4) Prediction of service life (5) Correlation of artificial and natural weathering.

What is claimed is:

1. A method for the non-destructive, in-situ assessment of a resilient elastic substrate, said method comprising the steps of:

providing a hand-held testing assembly having at least a detector means, actuating means, a prompting means, and processing means;

applying said detector means to a surface of said substrate;

urging said detector means into said substrate at a substantially constant speed;

holding said detector means at said predetermined depth for a first predetermined period of time;

releasing said detector means, allowing elastic recovery of said substrate;

maintaining detector means in engagement with said surface of said substrate during said releasing step for a second predetermined period of time in order to measure a rate of change of elastic recovery of said substrate;

receiving a prompt from said prompting means indicating said second predetermined period of time has elapsed; and processing compressibility and elastic recovery information of said substrate during said urging, holding, and releasing steps.

2. The method according to claim 1, wherein said detector means is urged into said substrate at a speed of from about 0.3 to about 0.7 mm/s.

3. The method according to claim 2, wherein said detector means is urged into said substrate at a speed of about 0.5 mm/s.

4. The method according to claim 1, wherein said detector means is held at said predetermined length for a period at least about 5 seconds.

5. The method according to claim 1, wherein said predetermined length is no more than about 10 mm.

6. The method according to claim 5, wherein said predetermined depth is about 5 mm.

7. The method according to claim 1, wherein said releasing step comprises maintaining said detector means in engagement with said surface of said substrate for a period of at least about 5 seconds during elastic recovery of said substrate.

8. The method according to claim 1, further comprising, on removal of the detector means from the surface of said substrate, visually inspecting the surface of said substrate to which said detector means has been applied.

9. The method according to claim 1, wherein said substrate is a sealant in a wall joint.

10. An elastic recovery testing assembly for the non-destructive, in-situ assessment of a resilient elastic substrate, said assembly comprising:

detector means adapted to be applied to a surface of said substrate and urged into said substrate at a substantially constant speed and held in said substrate at a predetermined depth for a predetermined time;

actuating means for actuating said urging of said detector means into said substrate, and releasing said detector means while maintaining said detector means in engagement with said surface of said substrate for a predetermined period of time in order to measure the rate of change of elastic recovery of the substrate;

prompting means for indicating said predetermined period of time has elapsed; and processing means for storing and processing compressibility and elastic recovery of said substrate, wherein said assembly is a hand-held device.

11. The assembly according to claim 10, wherein said detector means is adapted to be urged into said substrate manually or automatically at a substantially constant speed of from about 0.3 to about 0.7 mm/s.

12. The assembly according to claim 11, wherein said detector means is adapted to be urged into said substrate at a substantially constant speed of about 0.5 mm/s.

13. The assembly according to claim 10, wherein said detector means is adapted to be held in said substrate at a depth of no more than about 10 mm.

14. The assembly according to claim 13, wherein said detector means is adapted to be held in said substrate at a depth of about 5 mm.

15. The assembly according to claim 10, wherein said actuating means is disengageable such that, in use when said actuating means is disengaged, said detector means is displaceable by said substrate due to elastic recovery of said substrate.

16. The assembly according to claim 10, further comprising visual assessment means for facilitating visual assessment of the surface of said substrate to which said detector means has been applied.

17. The assembly according to claim 16, wherein said visual assessment means comprises a microscope unit mounted on said assembly.

18. The assembly according to claim 10, wherein said detector means comprises a detector head which contacts said surface of said substrate, and a piston shaft adapted to be engaged by said actuating means and for urging said detector head into said substrate.

19. The assembly according to claim 18, wherein said detector head is a brass pellet having a width of at least about 4 mm.

20. The assembly according to claim 10, wherein said actuating means comprises a piston load controller manually operable by a user of said assembly to urge said detector means into said substrate.

21. The assembly according to claim 10, further comprises prompting means for prompting a user of said assembly.

22. The assembly according to claim 21, wherein said prompting means comprises an electronic display.

23. The assembly according to claim 10, wherein said processing means comprises an electronic transducer or potentiometer which engages said detector means and a load cell which allow instantaneous detection of compressibility and elastic recovery of said substrate.

* * * * *